United States Patent [19]

Borsanyi et al.

[11] 4,278,092
[45] Jul. 14, 1981

[54] PERITONEAL CATHETER

[75] Inventors: Alexander S. Borsanyi, Corona del Mar, Calif.; Peter Ivanovich, Wilmette, Ill.; Urte Vaughan, Denver, Colo.

[73] Assignee: American Hospital Supply Corporation, Evanston, Ill.

[21] Appl. No.: 54,709

[22] Filed: Jul. 5, 1979

[51] Int. Cl.³ ............................................. A61M 25/00
[52] U.S. Cl. .............................. 128/348; 128/213 A; 128/DIG. 26
[58] Field of Search ............... 128/213 A, 348, 350 R, 128/DIG. 26; 3/1.5

[56] References Cited

U.S. PATENT DOCUMENTS

| | | |
|---|---|---|
| 3,365,728 | 1/1968 | Edwards et al. |
| 3,371,352 | 3/1968 | Siposs et al. |
| 3,466,671 | 9/1969 | Siposs |
| 3,663,965 | 5/1972 | Lee et al. ............................. 128/348 |
| 3,752,162 | 8/1973 | Newash .............................. 128/348 |
| 3,821,957 | 7/1974 | Riely et al. ......................... 128/348 |
| 3,903,895 | 9/1975 | Alley et al. .................. 128/DIG. 26 |
| 3,996,623 | 12/1976 | Kaster ..................................... 3/1.5 |

OTHER PUBLICATIONS

"Peritoneal Dialysis-. . . "; Jones et al.; Amsect Proceeding; vol. II; 1974.

Primary Examiner—Bradley Garris
Attorney, Agent, or Firm—Tilton, Fallon, Lungmus et al.

[57] ABSTRACT

A two-section implantable catheter for peritoneal dialysis is disclosed, the catheter having a retainer section which permanently ingrows into the abdominal wall and a catheter tube section. The two sections are normally connected together in a fluid-tight seal but may be separated to permit replacement of the tube section of an indwelling catheter without necessitating surgical removal of the retainer section.

12 Claims, 5 Drawing Figures

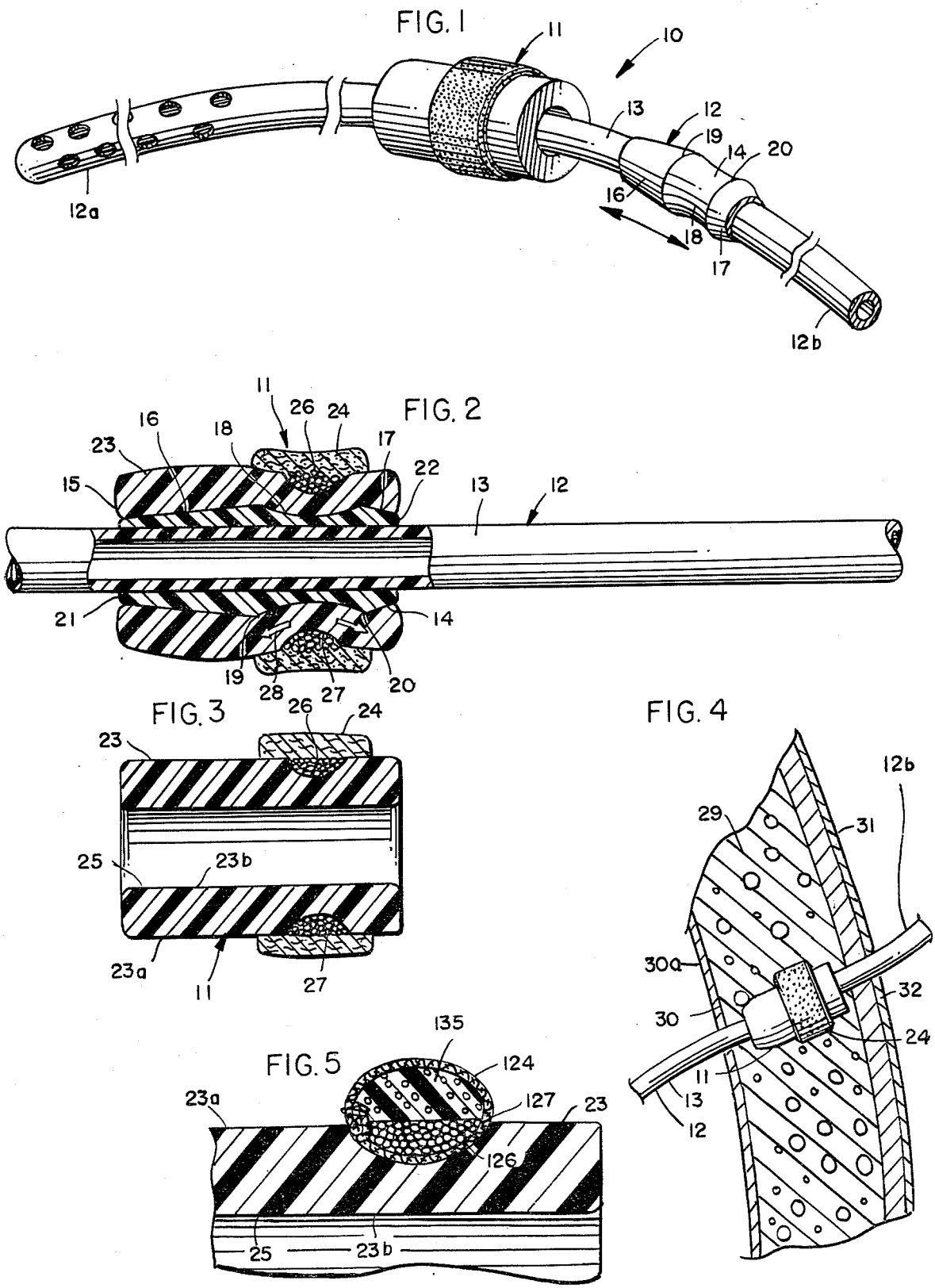

PERITONEAL CATHETER

BACKGROUND AND SUMMARY

In peritoneal dialysis, dialysate is introduced into the peritoneal cavity through an indwelling catheter and, after a measured interval during which dialysis occurs within the patient with the peritoneal membrane serving as the diffusion membrane, is removed and discarded. Such a procedure has a number of advantages over conventional hemodialysis, such as the elimination of intravenous conditions, avoidance of the risks and complexities of external blood circulation, and the suitability of the procedure for patient self-treatment. In general, peritoneal dialysis is gaining recognition as a relatively simple, safe, and inexpensive alternative to hemodialysis. See K. M. Jones and P. Ivanovich, Peritoneal Dialysis-Treatment for End-Stage Diabetic Nephropathy, AmSect Proceedings, Vol. II, pp. 97–99 (1974).

The indwelling catheter commonly used in peritoneal dialysis is perforated at its distal end and is provided with at least one porous cuff of Dacron or other material suitable for tissue ingrowth and secured to the catheter tube at an intermediate location. The short proximal end portion of the catheter projects externally from the patient's abdominal wall and is adapted to be connected to conventional external dialysis equipment when a lavage procedure is to be undertaken. Such a catheter, although intended to be a permanent or at least a long-term implantation, may require surgical removal after only a few months of use should the lumen of the catheter become occluded by fibrin, or should the openings at the distal end become clogged or reduced to such an extent that the rate of flow of dialysate becomes unacceptably low. Since such problems develop well after tissue ingrowth into the cuff (or cuffs) of the catheter has occurred, replacement of the ingrown occluded catheter requires an operating room procedure. Not only is such surgery bothersome and costly; it is also unpleasant both physically and psychologically for the patient.

A main object of this invention therefore lies in providing a peritoneal catheter construction which substantially eliminates occlusion of the perforations and/or lumen of an indwelling catheter as a major problem in chronic peritoneal dialysis. More specifically, this invention is concerned with an improved indwelling catheter that may be replaced when necessary, to overcome problems of catheter occlusion, without the need for major surgery and without the physical and emotional disadvantages attending such surgery.

In brief, the peritoneal catheter of this invention is formed in two main sections which are normally connected together in fluid-tight relation but which may be separated should occlusion of the catheter take place. One of the sections, the retainer section, comprises a tubular sleeve equipped with an external porous fabric cuff for tissue ingrowth. The other section, the catheter tube section, normally extends through the bore of the retainer section and is releasably coupled thereto. The catheter tube section is provided with a rigid tubular plug sealingly bonded thereto, the plug having an external annular recess and being receivable in the bore of the sleeve so that an inward annular projection of the sleeve is received within the recess to produce a snug fluid-tight interfit between the parts.

In the disclosed embodiment, the sleeve is resilient and is reinforced in the zone of the inward annular projection by multiple windings extending about the sleeve and concealed by the ingrowth ring or cuff. The tension of the winding may be varied according to the resilience of the sleeve material, and the thickness of that material, to produce an effective seal and still provide a separable interconnection between the two sections of the catheter.

Other features, advantages, and objects of the invention will become apparent from the specification and drawings.

DRAWINGS

FIG. 1 is a perspective view of a peritoneal catheter embodying this invention.

FIG. 2 is a fragmentary longitudinal sectional view of the catheter with the sections in assembled condition.

FIG. 3 is a fragmentary longitudinal sectional view of the retainer section with the tube section removed therefrom.

FIG. 4 is a generally horizontal sectional view illustrating the catheter extending through the abdominal wall of a patient.

FIG. 5 is a sectional view illustrating a variation of the sleeve and cuff construction of the retainer section.

DESCRIPTION OF PREFERRED EMBODIMENT

Referring to the drawings, the numeral 10 generally designates a peritoneal catheter consisting essentially of two main sections, namely, a retainer section 11 and a catheter tube section 12. The tube section has a perforated distal end 12a and a proximal end 12b suitable for connection to any standard peritoneal dialysis machines such as, for example, the Drake-Willock unit marketed by D.W.S. Inc., Portland, Oregon or the Physio-Control unit marketed by Physio-Control Corporation, Redmond, Washington. Such units are well known in the art and, since they are not part of the present invention and are disclosed in the aforementioned reference, further discussion of them is believed unnecessary herein.

The catheter tube 12 includes a soft plastic tube 13 and a relatively rigid tubular plug member 14 externally secured to tube 13 at an intermediate point closer to the tube's proximal end. Tube 13, without plug 14, is substantially the same as the standard peritoneal catheter developed by H. Tenckhoff and H. Schechter, as disclosed in the aforementioned Jones-Ivanovich publication and in certain of the references cited therein. The tube 13 may be formed of any relatively soft elastomeric material which is non-irritating and generally compatible with body tissue. Silicone rubber has been found particularly effective but other materials having similar properties may be used. In general, the material should have a durometer within the range of about 30 to 60 Shore A. The dimensions of the tube may vary considerably depending on the size of the patient and other factors but, in general, the length would normally fall within the range of about 25 to 100 centimeters, the inside diameter within the range of about 2 to 5 millimeters, and the wall thickness within the range of approximately 0.5 to 1.0 millimeters.

The tubular plug 14 is permanently secured to the tube 13 by a silicone adhesive 15 or by any other suitable means. As shown in FIGS. 1 and 2, the outer surface of the plug includes a tapered distal portion 16, a tapered proximal portion 17, and an intermediate annular recess or channel 18. The recess is arcuate when viewed in longitudinal section and is delimited by a pair of longitudinally-spaced ridges 19 and 20 which define the largest outside cross sectional dimensions of the plug. It will also be observed that the plug has annular end faces 21 and 22, resulting from the fact that the frusto-conical surfaces 16 and 17 have dimensions at their reduced ends which are still substantially larger than the outside diameter of tube 13 and that the edges defining those end faces, as well as the edges defining the end faces of the tubular retainer 11, are rounded to avoid sharp edges and to allow smooth insertion and removal of the plug.

The plug may be formed of any rigid and durable material that is tissue-compatible and is capable of being permanently secured to tube 13. A polycarbonate condensation product marketed under the designation Lexan has been found particularly effective, but other suitable materials having similar properties may be used. Rigidity and strength are important because the plug must be capable of withstanding the constrictive force exerted by the retainer 11 to produce a fluid-tight bacterial barrier between the parts when they are assembled as shown in FIG. 2.

The retainer 11 includes a tubular sleeve 23 and a porous ring or cuff 24 for tissue ingrowth. In the illustration given, the sleeve is formed entirely of a resilient polymeric material such as, for example, soft silicone rubber. When the sleeve is in an untensioned or undeformed state, its concentric outer and inner surfaces 23 and 23b may be generally cylindrical in configuration as shown. Thus, the bore 25 defined by inner surface 23b is of substantially uniform diameter, that diameter being the same or only slightly greater than the outside diameter of plug 14 at the reduced ends thereof. Therefore, when the end-tapered plug is inserted into the bore of the sleeve, considerable outward deformation of the stretchable sleeve takes place.

Means are provided to limit or control the extent of radial expansion of the intermediate portion of the sleeve, that is, the portion of the sleeve which extends about recess 18 when the plug is fully received within the sleeve. In the embodiment illustrated, such means takes the form of a filamentary winding 26 disposed within an external channel 27 formed in the intermediate portion of the sleeve although it is believed apparent that a relatively non-stretchable collar or band of metal or other suitable material might be substituted for the winding. Where a winding is used, the filament may be formed of Dacron or any other suitable material having high tensile strength and may, if desired, be embedded in a matrix material such as, for example, a silicone cement. Such winding serves as a reinforcing element to limit the extent of radial displacement of the intermediate portion of the sleeve when the plug is inserted. The material of the sleeve that would otherwise expand outwardly is urged axially or longitudinally as indicated by arrows 28 in FIG. 2. The result is a fluid-tight seal between the opposing surfaces of the intermediate portions of the sleeve 23 and plug 14. When the plug is fully inserted within the sleeve, as depicted in FIG. 2, it is believed apparent that the force necessary to extract the plug will progressively increase until the ridge 19 of the plug clears the intermediate portion of the sleeve. Similarly, further insertion of the plug would be met by increased resistance until ridge 20 advances distally beyond the sleeve's intermediate portion. Consequently, the plug resists uncoupling movement, the extent of such resistance depending largely on the tightness and mass of winding 26 and the respective dimensions of plug 14 and sleeve 23. The objective is to wind the filament 26 just tightly enough that the plug could not under any normal circumstances become accidentally disconnected from the sleeve while, at the same time, permitting such disconnection when replacement of the catheter tube 12 is desired. If the characteristics of the elastomer selected for sleeve 23 are such that the sleeve does not readily expand as the plug is inserted, the cylindrical shape of the inner surface of the sleeve may be modified to conform (when the sleeve is untensioned) at least partially to the conical shape of the plug, thereby reducing the forces required for plug insertion.

The porous cuff 24 may be formed of a felt, foam, or multiple layers of any suitable material having sufficient porosity, strength, and tissue-compatability to permit the ingrowth of tissue when the catheter is surgically implanted. A felt of Dacron or other appropriate material is shown in FIGS. 2 and 3, such material being adhesively secured to the outer surface of the sleeve 23 over winding 26. If desired, the same adhesive which serves as a matrix for winding 26 may also be used to join the sleeve and cuff.

FIG. 4 schematically depicts the catheter 10 in implanted condition. It will be observed that the retainer 11 is located within a layer 29 of subcutaneous fat of the abdominal wall between peritoneal membrane 30 (and preperitoneal facia 30a) and the dermis and epidermis 31 and 32. The distal end portion 12a of the catheter tube is disposed within the peritoneal cavity and the proximal end portion of that tube projects externally from the abdominal wall. A surgical procedure is obviously required in order to implant the catheter and, following such implantation, tissue invades the ingrowth ring 24 to secure the catheter in place. Healing occurs in the inner and outer layers 30–32 about tube 13, although no ingrowth of tissue into the smooth flexible tube is possible.

Should replacement of the catheter tube 12 later become necessary because of proteinaceous occlusion of the perforations and/or lumen of the catheter, such replacement may be readily achieved without disrupting or disturbing the connection between the body tissue and ingrowth ring 24. While a small external incision may be necessary in order to allow the tapered plug to be withdrawn from the sleeve and through dermis and epidermis 31 and 32, such an incision would only be a relatively simple step involving far less discomfort and trauma to the patient than surgical removal of the entire catheter, including retainer 11. Following such removal of the catheter tube 12, a new sterile catheter tube of matching dimensions would be fitted into place for subsequent peritoneal dialysis of the patient.

FIG. 5 illustrates an alternate form of ingrowth ring that may be used in place of the ring shown and described in connection with FIGS. 1–4. Ring 124 is formed in a manner similar to the sewing rings of prosthetic heart valves, as disclosed generally in patents such as U.S. Pat. Nos. 3,466,671, 3,371,352, and 3,365,728. The ring is formed of a suitable fabric such as, for example, Dacron cloth, and is folded into channel 127 where it is held in place by winding 126. The winding therefore performs the dual functions of holding the ingrowth cuff in place within the channel and of limiting radial expansion of sleeve 23 in the manner already described. If desired, the interior of the cuff 124 may be occupied by a resilient foam pad 135 or, if desired, by multiple folds of cloth 124.

While in the foregoing we have disclosed embodiments of the invention in considerable detail for purposes of illustration, it will be understood by those skilled in the art that many of these details may be varied without departing from the spirit and scope of the invention.

We claim:

1. A peritoneal catheter including a tube section and a retainer section, said tube section comprising an elongated flexible plastic tube for delivering and withdrawing dialysate and a relatively rigid tubular plug permanently secured to and extending about an intermediate portion of said tube, said plug having tapered longitudinal surfaces adjacent the ends thereof and having an annular recess between said tapered surfaces, said retainer section comprising a resilient sleeve having a bore for sealingly and releasably receiving said plug and having a porous resilient tissue ingrowth ring secured to the outer surface of said sleeve, whereby, following a term of implantation of said catheter, said tube section may be removed from a patient for cleaning or replacement without necessitating removal of said retainer section and without disturbing the ingrowth of tissue into said ring.

2. The catheter of claim 1 in which said sleeve has a bore of generally cylindrical configuration.

3. The catheter of claim 2 in which said bore has a diameter approximating the outside diameter of said plug at the ends thereof.

4. The catheter of claim 2 in which said sleeve is formed of silicone rubber.

5. The catheter of claim 1 in which reinforcing means of limited expandability extends about the portion of said sleeve receiving said annular recess of said plug when said tube section and said retainer section are fully assembled.

6. The catheter of claim 5 in which said reinforcing means comprises a filamentary winding.

7. The catheter of claim 6 in which said winding also secures said ingrowth ring in place.

8. A peritoneal catheter including a tube section and a retainer section, said tube section comprising an elongated flexible plastic tube for delivering and withdrawing dialysate and a relatively rigid tubular plug permanently secured to and extending about an intermediate portion of said tube, said plug having tapered longitudinal surfaces adjacent the ends thereof and having an annular recess between said tapered surfaces, said retainer section comprising a resilient sleeve having a generally cylindrical bore for sealingly and releasably receiving said plug and having a porous resilient tissue ingrowth ring secured to the outer surface of said sleeve, said sleeve being provided with reinforcing means of limited expandability in the portion thereof extending about said annular recess of said plug when said tube section and retainer section are fully assembled.

9. The catheter of claim 8 in which said bore of said sleeve has a diameter that approximates the outside diameter of said plug at the ends thereof.

10. The catheter of claim 9 in which said sleeve is formed of silicone rubber.

11. The catheter of claim 8 in which said reinforcing means comprises a filamentary winding extending about said sleeve.

12. The catheter of claim 11 in which said winding also secures said ingrowth ring in place on said sleeve.

* * * * *